US006573106B1

(12) United States Patent
Matson

(10) Patent No.: US 6,573,106 B1
(45) Date of Patent: Jun. 3, 2003

(54) METHOD OF TREATING CARBON OR GRAPHITE TO INCREASE POROSITY AND PORE UNIFORMITY

(75) Inventor: Wayne R. Matson, Ayer, MA (US)

(73) Assignee: Esa, Inc., Chelmsford, MA (US)

( * ) Notice: Subject to any disclaimer, the term of this patent is extended or adjusted under 35 U.S.C. 154(b) by 0 days.

(21) Appl. No.: 09/344,933

(22) Filed: Jun. 28, 1999

Related U.S. Application Data

(62) Division of application No. 08/975,163, filed on Nov. 20, 1997, now abandoned.

(51) Int. Cl.$^7$ .............................. C09C 1/44; C09C 1/46; C01B 31/08; C01B 31/10; C01B 31/12
(52) U.S. Cl. ...................... 436/183; 205/646; 423/460; 502/416
(58) Field of Search .................. 436/161, 178, 436/183; 422/69, 70; 423/445 R, 448, 449.1–449.4, 460; 205/646; 502/416

(56) References Cited

U.S. PATENT DOCUMENTS

| | | | |
|---|---|---|---|
| 3,855,099 A | | 12/1974 | Matson |
| 4,140,599 A | * | 2/1979 | Yamasaki et al. |
| 4,263,268 A | | 4/1981 | Knox et al. |
| 4,404,065 A | | 9/1983 | Matson |
| 4,413,505 A | | 11/1983 | Matson |
| 4,465,576 A | * | 8/1984 | Negishi et al. |
| 4,484,252 A | * | 11/1984 | Ruijgrok et al. |
| 4,500,432 A | | 2/1985 | Poole et al. |
| 4,552,013 A | | 11/1985 | Matson |
| 4,704,196 A | * | 11/1987 | Saito et al. |
| 4,804,455 A | | 2/1989 | Matson |
| 4,812,344 A | | 3/1989 | Jaeger et al. |
| 4,976,994 A | | 12/1990 | Matson |
| 5,011,608 A | | 4/1991 | Damjanovic |
| 5,032,240 A | | 7/1991 | Argade |
| 5,063,064 A | | 11/1991 | Bourbon et al. |
| 5,098,576 A | | 3/1992 | Cabrera et al. |
| 5,252,333 A | | 10/1993 | Horrobin |
| 5,287,383 A | * | 2/1994 | Hirai |
| 5,358,802 A | | 10/1994 | Mayer et al. |
| 5,444,031 A | * | 8/1995 | Hayden |
| 5,834,114 A | * | 11/1998 | Economy et al. |

FOREIGN PATENT DOCUMENTS

| | | |
|---|---|---|
| EP | 0042683 | 12/1981 |
| EP | 0365327 | 4/1990 |

OTHER PUBLICATIONS

Chemical Abstracts No. 120:145390, Leboda et al., Manufacturing activated carbon, especially for chromatography, Polish Patent No. 161084.*
Pilger et al, Assay for the determination of urinary 8–hydroxy–2'–deoxyguanosine by High–performance liquid chromatography with electrochemical detection, Journal of Chromatography B, 689 (1997) pp 399–403.
Xie et al., Current Separations, 131(1), pp. 18–21.
Chemical Abstracts, DN 98:175747, Stulik et al., J. Chromatoger., 273(1) pp. 77–86.
Webster's Ninth New Collegiate Dictionary, Merriam Webster Inc., Springfi MA (1987), p. 227.
Shigenaga et al., Methods Enzymol. (1990), 186 (Oxygen Radicals Biol. Syst., PtB), pp 521–30.
Teuxeura et ak., Anal. Biochem. (1995), 226(2), pp 307–19.

* cited by examiner

Primary Examiner—Jan Ludlow
(74) Attorney, Agent, or Firm—Hayes Soloway P.C.

(57) ABSTRACT

A method of pre-treating carbon or graphite material to increase porosity and render pore size more uniform includes etching by electrochemically pulsing the material in an acid saline solution and optionally steam treating.

20 Claims, 4 Drawing Sheets

METHOD OF TREATING CARBON OR GRAPHITE TO INCREASE POROSITY AND PORE UNIFORMITY

This is a divisional of application Ser. No. 08/975,163 filed on Nov. 20, 1997 now abandoned.

FIELD OF THE INVENTION

The present invention relates to improvements in analytical techniques. The invention has particular utility in connection with determination of low levels of analytes in highly complex mixtures, and will be described in connection with such utility, although other utilities are contemplated.

BACKGROUND OF THE INVENTION

The determination of very low levels of specific analytes in complex mixtures of hundreds of possible interferences is a classical problem in analytical chemistry. For example, in recent developments in the assessment of oxidative stress and in the assessment of genetic damage from inherited and environmental factors, the measurement of urinary 8 hydroxy 2' deoxyguanosine (8OH2'dG) and other similar purine and pyrimidine indicators of DNA damage has developed as a potentially useful diagnostic therapy directing tool. These measurements have been used in clinical research in the areas of neurological disorders, cardiovascular problems, cancer, and assessment of biological environmental risk.

The overall utility of such measurements is compromised, however, by the lack of reliable measuring technology that will allow the intercomparison of values among different laboratories and studies. While several methods incorporating multiple separations and finally analytical techniques of liquid chromatography with electrochemical detection or gas chromatography, or mass spectroscopy have been published, they all suffer from problems of reliability, certainty of the analyte measured, complexity of preparation and manipulation, short and long term accuracy and precision, and cost. One of the most commonly cited techniques has been liquid chromatography with electrochemical detection employing a variety of preparation and concentration procedures and/or automated column switching. In automated column switching a portion of the eluent band from a first column is trapped in an injection loop and then transferred to a second column with different characteristics of separation. While some researchers reportedly have obtained reliable information with these techniques, the procedures are both fragile and prone to individual specific errors. This is because of the small non-quantitative and variable amounts trapped from the band and from the first column (typically less than 10%), and because of the highly variable nature and high level of interfering species at the typical levels of ca 5 ng/ml of analyte of interest.

OBJECT OF THE INVENTION

It is thus an object of the invention to overcome the aforesaid and other disadvantages of the prior art. Another object of the present invention is to provide an analytical technique for determining low levels of analytes in complex mixtures. A more specific object of the invention is to provide an analytic technique for analyzing 8 hydroxy 2' deoxyguanosine in biological samples.

BRIEF DESCRIPTION OF THE INVENTION

In order to effect the foregoing and other objects of the invention, in accordance with the present invention, there is provided a sample pre-separation and concentration system comprising a plurality of trapping columns having a high selectivity for classes of compounds of interest, upstream of a standard separation column. For example, as applied to the analysis for 8OH2d'G in urine and other biological samples, the basis of the invention is the replacement of the injection loop from the first column with one or more small porous carbon columns that have a very highly selectivity for purines, and certain other classes of compounds such as aromatic amines and nitro compounds and certain flavones flavenoids and other highly conjugated species. These columns have sufficient selectivity that they can trap essentially the entire eluting band containing the analyte of interest in a very small, e.g. 20–250 ul volumes, and then be flushed for a relatively long time by a second eluting buffer to remove almost all species but the analyte of interest. The porous carbon column is then switched to the head of a second separation column employing a buffer identical to the flushing buffer except for a displacing agent that strips the analyte of interest from the carbon in a sharp peak that is compatible with optimum separation characteristics of the second column. By way of example, for 8OH2'dG, the displacing agent of preference is Adenosine, a compound of similar structure but not electroactive. The principle of similarity by non-detectability is general for the third buffer additive. For example, phenylalanine may be used to displace nitrotyrosine.

BRIEF DESCRIPTION OF THE DRAWINGS

For a further understand of nature and objects of the present invention, presence should be had to the following detailed description taken in conjunction with the accompanying drawings wherein.

DETAILED DESCRIPTION OF THE INVENTION

Further understanding of the features and advantages of the present invention will be had from the following detailed description of the invention, which illustrates the analysis of 8 hydroxy 2' deoxyguanosine (8OH2'dG) in urine. It will be understood, however, that the invention advantageously may be employed for analyzing other analytes in complex mixtures.

Figure 2:
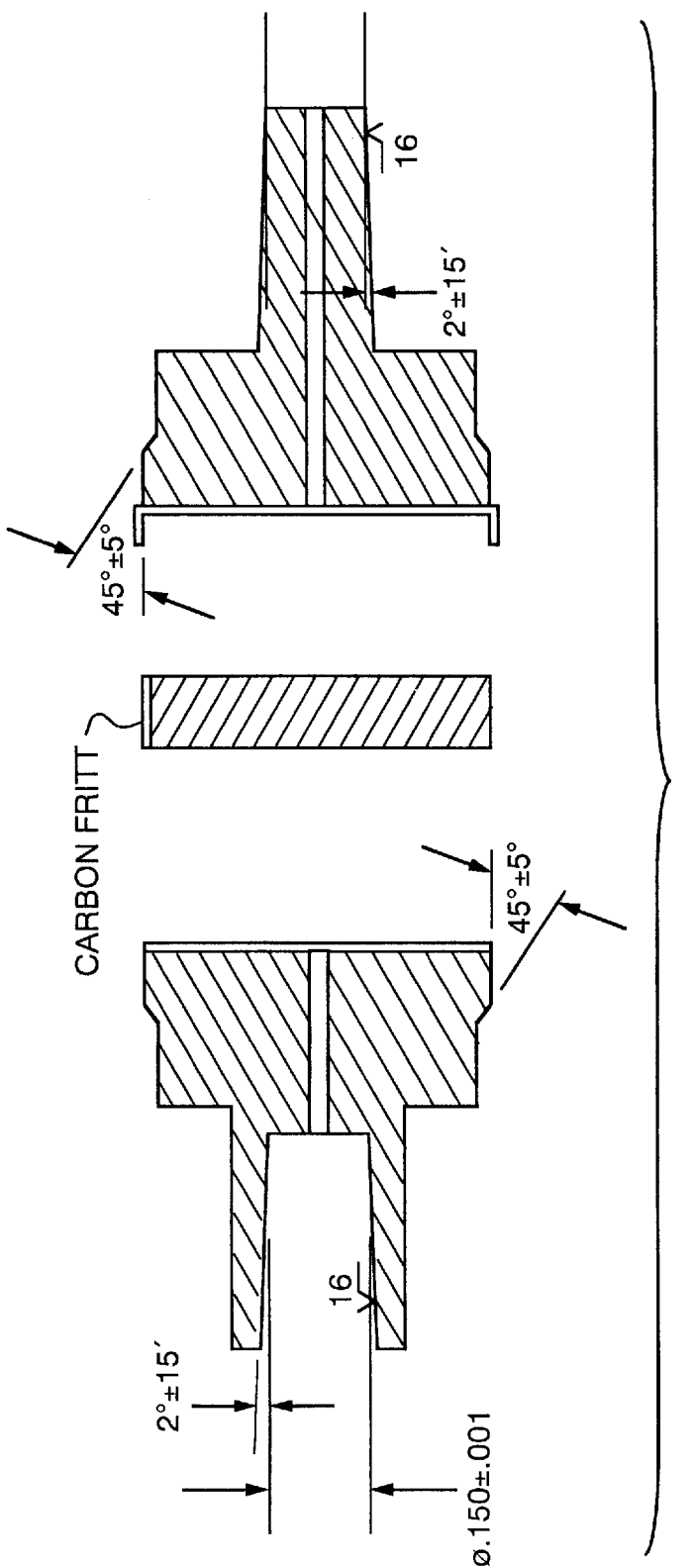
FIG. 2 is a side elevational view, in cross section, showing details of a preferred form of sample preparation column useful in accordance with a preferred embodiment of the present invention.

A key feature and advantage of a preferred embodiment of the invention involves the use of unique carbon packed cells for separating and concentrating analytes of interest. In order to insure essentially one hundred percent trapping of the analyte of interest in very small volumes, two technical problems have been addressed. One critical design and construction issue for carbon packed cells is the sealing of the edge of the carbon cylinder in such a way that no flow path can be established that does not go through the mass of the carbon and that the carbon is not crushed. For carbon packed cells of either separate particles or sintered carbon material which operate at relatively low pressures of 5–15 bar this can be achieved by diverse techniques. For example, (as in FIG. 2) heat shrink tubing, microwaving of pressfit parts and ultrasonic welding of pressfit parts are all acceptable techniques. However, for columns which have to operate up at higher pressures, e.g. 100–400 bar, the design and construction process is more complex. To accomplish this in accordance with one embodiment of the invention, a chemically inert plastic sleeve under compression operating essentially as a highly viscous fluid is employed. The plastic characteristics necessary are chemical inertness and a compression deformation point below the typical 10,000 psi deformation point of the porous carbons. A low creep rate at room temperature and a high coefficient of thermal expansion is also desirable. A range of high molecular weight linear polyethylenes are commercially available and advantageously may be employed.

Figure 3:
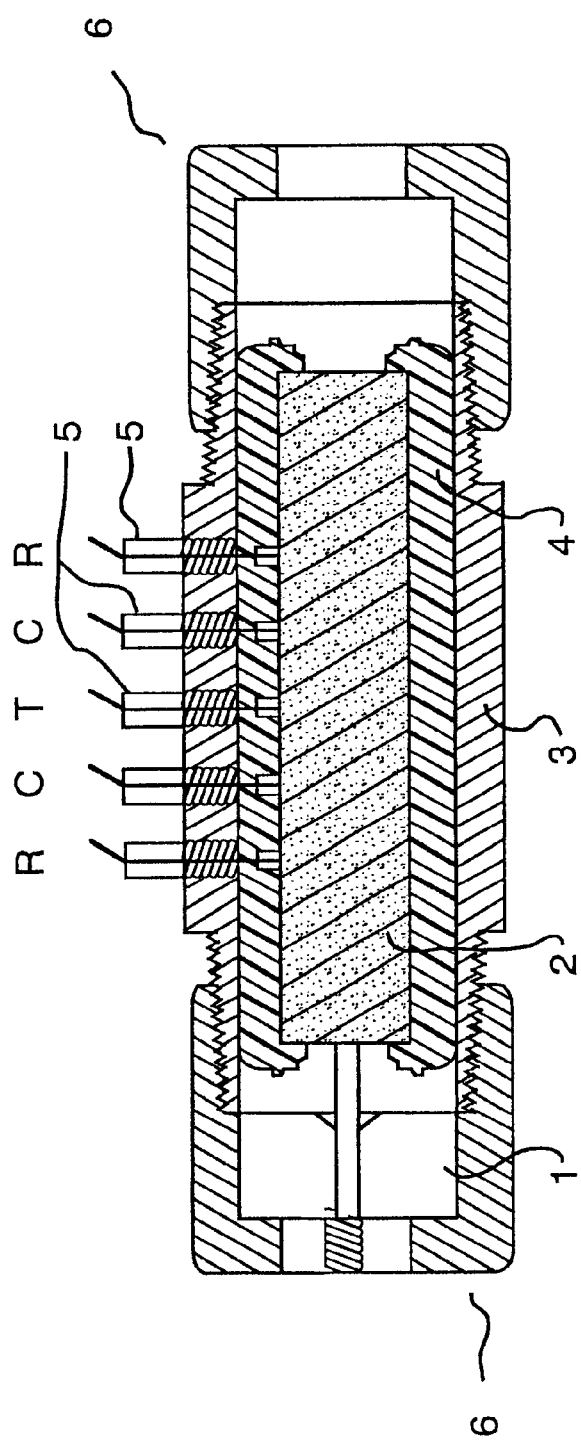
FIG. 3 is a side elevational view, in cross section, of a separation and/or testing column controlled as an electrochemical cell useful in accordance with a preferred embodiment of the invention.

High pressure resistant packed carbon cells, useful as pre-separation cells in accordance with the present invention, are prepared as follows: Referring to FIG. 3, cylindrical carbon frits 2 are inserted into a plastic sleeve 4 of 0.505 I.D. inch diameter. Plastic sleeve 3 is formed of a high molecular weight linear polyethylene preferably with a melt point of 128° C., and having compression deformation point of 9000 psi and a coefficient of expansion of 5.1 in/in/° C. The assembly then is cooled in dry ice acetone. After insertion into the dry ice acetone, end pieces 6 formed of another chemically inert plastic material, and having a lower coefficient of expansion than the coefficient of expansion of the plastic sleeve 4 for example, polyether ether ether ketone (PEEK) are assembled onto sleeve 4, and tightened to the point of touching the carbon, and the assembly is then removed from the dry ice acetone. (The cooled resulting assembly is then inserted in a metal sleeve 3 of 0.500 I.D. inch diameter.) The assembly is capped and allowed to warm to room temperature. When the piece comes to room temperature, the differential expansion of the polyethylene sleeve as compared to the PEEK fittings and the metal retaining sleeve seals the fittings to the sleeve and brings the internal pressure of the assembly to ca8-9000 and maintains the seal at about 6000 psi internal pressures that are the maximum expected in chromatographic separations.

Another critical design characteristic is the selection of the base porous carbon material and the treatment of the carbon to achieve a balance of desired characteristics. These characteristics include:

1. Low back pressure,
2. A high number of theoretical plates,
3. Control of the oxidizing and reducing potential of the surface,
4. High capacity for adsorption, and
5. High and specific selectivity for different classes of compounds.

Characteristics 1 and 2 are in opposition. A high number of plates implies typically a small pore size which implies a high back pressure. Optimization is achieved at any pore size by having highly uniform pores and as small an amount of supporting matrix (as large a number of pores as possible). In the current invention this is achieved as follows: First, attention is given to selection of the base carbon material. We have found that $8\mu$ to $12\mu$ particle size carbon sintered into a cohesive material with $0.5-1\mu$ pore size works best. In this regard, we have selected carbon available from Poco Union Carbide Inc. under the designation PS2. With suitable cleaning, this material can be used directly to advantage. However, in order to improve performance, we also pre-condition the carbon by selectively etching the material to make the pore size more uniform and increase the net porosity. Selective etching can be accomplished by either of two processes with essentially equivalent results. One process involves electrochemically pulsing the carbon in an acid saline solution. Preferably, the carbon is subjected to pulsing at 0–1.4V. vs. SCE in a saturated saline solution of 1–2 M in HCl for 24–48 hours. The other process utilizes a modification of the water gas reaction in which the carbon is heated in an oxygen free steam atmosphere, e.g. at 370–480° C. for 24–240 hours. In the first case the etching is controlled by monitoring the total coulombs passed during the process and by monitoring the increase in capacitive current. In the second case by monitoring the volume of the H2 and CO produced in the reaction. Both processes significantly increase the uniformity of the pores, and thus the capacity of the carbon materials, reduce the back pressure and increase somewhat the number of separation plates. Both processes can be used in series, and also advantageously may be employed to pre-condition bulk carbon and graphite that is not initially highly porous.

The control of the redox status of the carbon is critical both because of the possibility of loss of a fragile analyte by oxidation and because the redox potential has a significant effect on the selectivity and retentivity of particular analytes. This can be achieved initially by the control of the selective etching process. The water gas reaction creates inherently a reductive surface ca –0.2 v vs a SCE and the electrochemical process can be held at a reducing potential after completion to achieve the same effect. Control of the redox potential can periodically be maintained for 2–8 days by chemical poising with such agents as ascorbate, borohydride or dithiothriotol. Activation and control of redox potential for the single use packed carbon cells can be established initially for production purposes by bulk refluxing of the carbon in propanol HCl. For more precise control of the redox potential of the columns, the carbon is controlled as a test electrode as shown in FIG. 3. Control of redox potential whether chemical or electrochemical controls the selectivity of certain compounds. Reducing potentials of –100–0 mv vs SCE give approximately twice the retention time for purines as potentials of 300–400 mv vs SCE.

Tests of the carbon packed cells utilizing 2D gel electrophoresis also indicate that the redox potential affects the retention of certain classes of proteins and large macromolecules.

Figure 1:
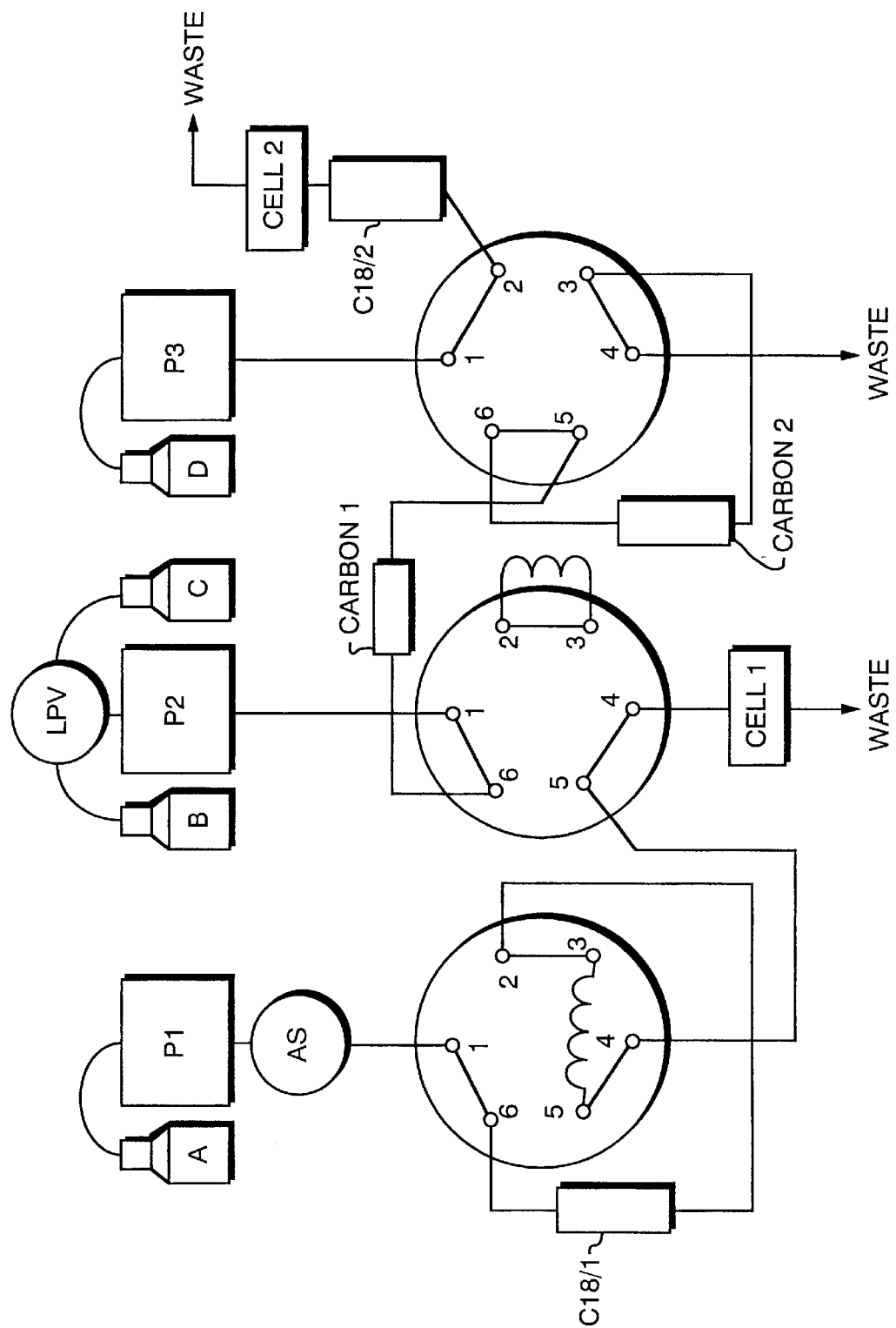
FIG. 1 is a schematic view of one form of sample separation and analysis system in accordance with the preferred embodiment of the invention.
Figure 4:
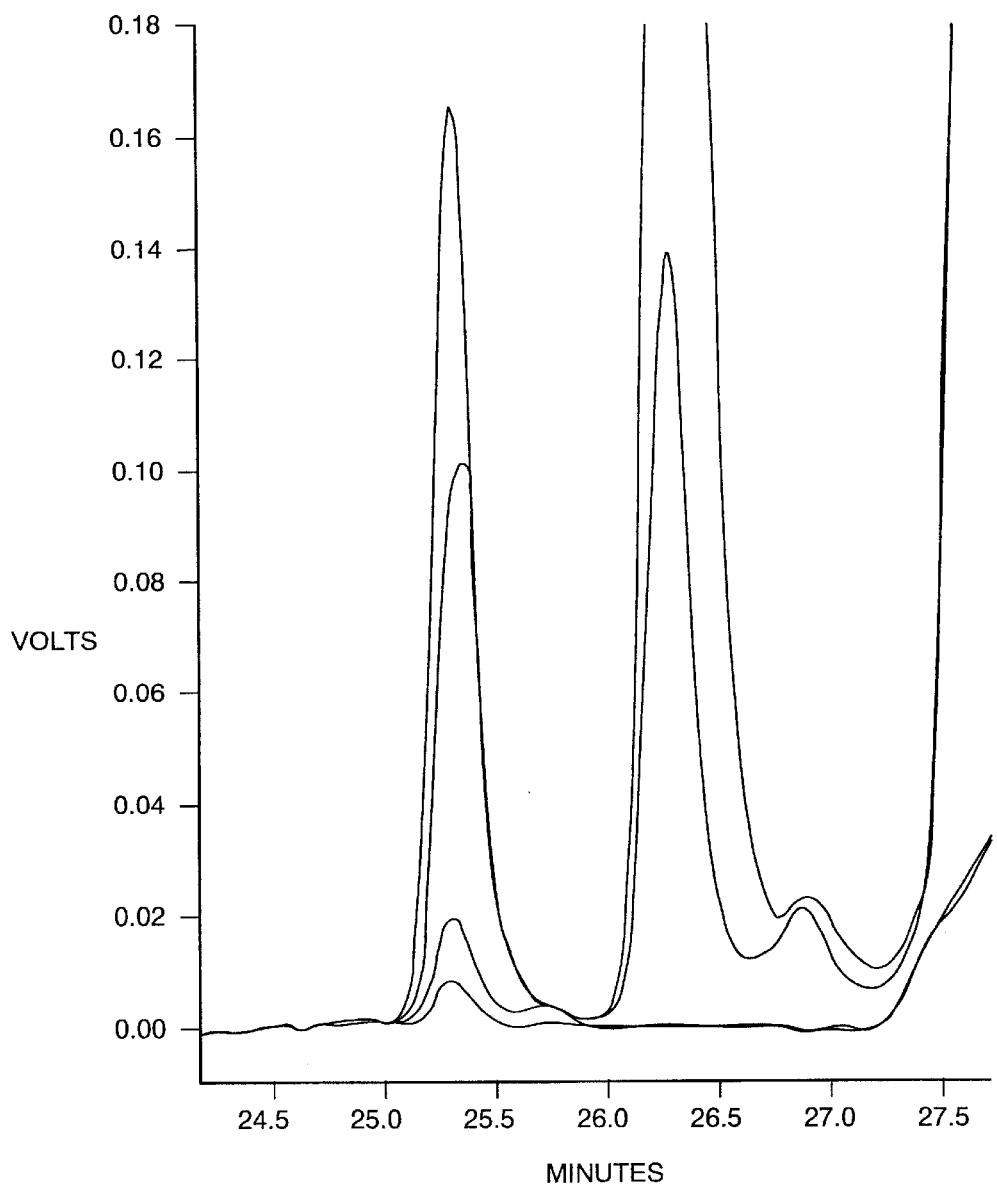
FIG. 4 is a series of graphs showing the current over time of an electrochemical analysis in accordance with the present invention.

The present invention, which provides a sample preparation and concentration system which may be fully automated, and if desired, integrated into a fully automated assay system, will now be described in connection with the separation and measurement of 8OH2'dG in urine. Referring in particular to FIGS. 1 and 4 of the drawings, the overall process is as follows:

Aqueous based buffers were provided as follows:

Buffer A: 4% Methanol, 0.1 M Lithium Acetate at pH 6.5, balance in water.

Buffer B: 4.5% Acetonitrile, 2% Acetic Acid, 0.1 M Lithium Acetate at pH 3.4, balance in water.

Buffer C: 90% Propanol, 5% Acetic Acid, 0.2 M Lithium Acetate, balance in water.

Buffer D: 4.5% Aceonitrile, 2% Acetic Acid, 0.2 M Lithium Acetate at pH 3.4, 1.5 G/l Adenosine and 500 ul/l of Buffer C.

Selection and composition of buffers is directed by several considerations. Buffer A should be neutral to slightly basic in order to be compatible with a dilution buffer that will dissolve particulates in the sample. Critical to the selection of the diluent is the dissolution of any particulate material precipitated from a urine sample which by co-precipitation mechanisms will contain a variable fraction of the 8OH2'dG. A secondary consideration is matching the ionic strength and organic modifier concentration of the buffer A to achieve long term stability of retention times on the first column. Buffer B and D should be exactly matched except for the carbon eluting compound and small additions of buffer C to buffer D in order to avoid large void effects and small baseline disturbances. Buffers B and D should be of sufficiently high organic modifier composition to clean the carbon of possible interferences in a reasonable time, and buffers B and D should contain a different organic modifier and be at a different pH from buffer A to enhance separation of any possible interferences. Buffer C should be of sufficient cleaning power to remove any residual poisoning agents from the carbon over extended periods of use. Finally, since low levels of organic modifier are involved, all buffers should be bacterio and fungistatic.

FIG. 1 shows the valving and switching setup for transferring various segments of the sample. The timing of events is begun from the injection of the sample by the autosampler AS onto the head of the first column C18/1 is as follows:

Time 0. CONDITION 1: c18/1 at a flow rate of 0.9 ml/min of buffer A delivered by pump P1; Carbon 1 and Carbon 2 at a flow rate of 1 ml/min of buffer B delivered through a low pressure switching valve LPV and pump P2; column C18/2 at a flow rate of 0.9 ml/min of buffer D delivered through pump P3.

Time 11.3–12.8 min CONDITION 2: valve 2 switches directing buffer A through C18/1 and carbon 1 and carbon 2.

Time 12.8–17.0 valve 2 switches back to condition 1 flushing the trapped band of sample on carbon 1 and carbon two with buffer B.

Time 13.2–29 min CONDITION 4 valve 1 switches to reverse the flow of buffer A through column C18/1.

Time 17.0–17.8 CONDITION 5 valve 3 switches to direct the flow of buffer D through carbon 2 onto column C18/2.

Time 17.8 valve 3 switches back to condition 4.

Time 18–29 l pv switches to deliver buffer C to carbon 1 and carbon 2 to clean the carbons and extend their longevity cycle between maintenance events.

Time 29–40 system in condition 1.

Time 40 initiate next cycle.

Cell 1 is a Model 5010 multiple electrode electrochemical detection cell, available from ESA, Inc. The cell comprises a multiple electrode coulometric cell, and is used for monitoring the output of column C18/1. It is used primarily for calibration of retention time and to measure major constituents in a sample either as a quality control measure or to obtain normalizing values for the primary analyte in the sample. Typical settings are T1 400 mv, T2 700 mv. Cell 2 is a series combination of an ESA Model 5020 conditioning cell, and an ESA Model 5011 analytical cell. The conditioning cell is typically set at 10 mv and the 5011 cell at T1 20 mv T2 180 mv.

FIG. 4 shows the typical output of an assay for a 1 ng/ml and 20 ng/ml 8OH2'dG calibration standard, a urine sample and the same sample augmented with 10 ng/ml of 8OH2'dG. Samples are prepared by dilution 1:1 with a two fold concentration of buffer A. Sixty-nine samples were run over two days including 48 samples, 5 calibration standards at 20 ng/ml, 4 duplicates 4 samples spiked at 10 ng/ml, 2 high and 2 low quality control pool urines, and a regression line set of 4 standards at 1, 3, 10 and 30 ng/ml. Values were calculated from bracketing 20 ng/mml standards at position 1, 18, 35, 52 and 69, duplicates and spikes are run 30 positions apart during the assay, and regression line standards at positions 17, 34, 51 and 68 are treated s samples. Over 6 runs, the typical precision of duplicate pairs at a level of 4 ng/ml is ±0.04 or 1% rsd, recoveries of spiked samples is 100%±1.8% rsd, low QC pools are 2.61±0.04, high AQC pools are 8.73±0.008, the precision of standards treated as duplicate pairs is 20.00±0.19, and the regression line slope is 0.998±0.005.

The invention is susceptible to modification. For example, the pre-treated porous carbon matrix made as above described advantageously may be used in an off-line sample preparation cartridge. By way of example, a disk of 0.5 in diameter 0.150 in thick pre-conditioned, packed carbon frit 50 was trapped in a non-contaminating polypropylene and polyethylene housing 52 adapted with a Luer type fitting 54. The resulting cartridge may be used either alone to trap a compound of interest from a sample, or in conjunction with a C18 or other solid phase extraction device to obtain a secondary level of separation. For example, for assay or urinary 8OH2'dG the following sample preparation protocol has been used:

1 ml of urine diluted 1:1 with pH8 0.1M Li Acetate (aqueous solution) is passed through a C18 solid phase separation device;

2 ml of 1% Methanol in water is passed through the C18;

1 ml of 12% Methanol in water is passed through the C18 and the packed carbon cell in series to elute the 8OH2'dG from the C18 and trap it on the packed carbon; and 2–3 ml of 12% Methanol in water is then passed through the packed carbon cell alone.

The 8OH2'dG is then eluted from the packed carbon with 500 ul of 0.003 g/ml Adeosine in the running buffer for a following LCEC assay. Optionally, the first 200 ul of the eluent can be discarded and the next 300 ul used for the assay.

Results from the off line assay are equivalent to those of the automated on line assay; however, because of the decreased discrimination of the C18 solid phase extraction vs. that of the first stage C18 column, there are more peaks that occur in the final chromatogram and more care must be taken to avoid and detect possible interferences.

Various changes may be made without departing from the spirit and scope of the present invention.

What is claimed is:

1. A method of pre-treating a carbon or graphite material for use in a subsequent chemical analysis of complex mixtures so as to increase net porosity of the material and render pore size more uniform, which comprises selectively etching the carbon or graphite material by electrochemically pulsing tie carbon or graphite material, in an acid saline solution, for 24–48 hours.

2. A method according to claim 1, wherein said electrochemical pulsing comprises subjecting the carbon or graphite material to timed pulses in a voltage or current controlled cell.

3. A method according to claim 2, wherein said time pulses comprise controlled anodic potential pulsing.

4. A method of pre-treating a carbon or graphite material for use in a subsequent chemical analysis of complex mixtures so as to increase net porosity of the material and render pore size more uniform, which comprises selectively etching the carbon or graphite material by electrochemically pulsing the carbon or graphite material in a saturated saline solution of 1–2 M in HCl.

5. A method of pre-treating a carbon or graphite material for use in a subsequent chemical analysis of complex mixtures so as to increase net porosity of the material, and render pore size more uniform, which comprises the steps in sequence of:
   (a) selectively etching the carbon or graphite material using deoxygenated steam; and
   (b) subjecting the carbon or graphite material from step (a) to timed pulses in a voltage or current controlled cell.

6. A method according to claim 5, wherein said timed pulses comprise controlled anodic potential pulsing.

7. A method according to claim 6, wherein said controlled anodic potential pulsing is conducted in an aqueous acidic solution.

8. A method according to claim 7, wherein said aqueous acidic solution comprises an acidic halide.

9. A method according to claim 8, wherein said carbon or graphite materials are subjected to timed pulses in an acid saline solution.

10. A method according to claim 9, wherein said acid saline solution comprises a saturated saline solution of 1–2 M in HCl.

11. A method according to claim 5, wherein said carbon or graphite material is subjected to timed pulsing for 24–48 hours.

12. A method according to claim 5, wherein said carbon or graphite material is heated in a deoxygenated steam atmosphere at 370° C.–480° C. for 24–240 hours.

13. A method of pre-treating a carbon or graphite material for use in a subsequent chemical analysis of complex mixtures so as to increase net porosity of the material, and render pore size more uniform, which comprises the steps in sequence of:
   (a) subjecting the carbon or graphite material to timed pulses in a voltage or current controlled cell; and
   (b) selectively etching the carbon or graphite material from step (a) using deoxygenated steam.

14. A method according to claim 13, wherein said timed pulses comprise controlled anodic potential pulsing.

15. A method according to claim 14, wherein said controlled anodic potential pulsing is conducted in an aqueous acidic solution.

16. A method according to claim 15, wherein said aqueous acidic solution comprises an acidic halide.

17. A method according to claim 13, wherein said carbon or graphite materials are subject to timed pulses in an acid saline solution.

18. A method according to claim 17, wherein said acid saline solution comprises a saturated saline solution of 1–2 M in HCl.

19. A method according to claim 13, wherein said carbon or graphite material is subjected to timed pulsing for 24–48 hours.

20. A method according to claim 13, wherein said carbon or graphite material is heated in a deoxygenated steam atmosphere at 370° C.–480° C. for 24–240 hours.

* * * * *

UNITED STATES PATENT AND TRADEMARK OFFICE
CERTIFICATE OF CORRECTION

PATENT NO. : 6,573,106 B1 Page 1 of 1
DATED : June 3, 2003
INVENTOR(S) : Matson

It is certified that error appears in the above-identified patent and that said Letters Patent is hereby corrected as shown below:

Column 6,
Line 53, "tie" should be -- the --.

Signed and Sealed this

Twenty-eighth Day of October, 2003

JAMES E. ROGAN
*Director of the United States Patent and Trademark Office*